United States Patent [19]

Mehl

[11] Patent Number: 4,976,269
[45] Date of Patent: Dec. 11, 1990

[54] TISSUE NEEDLE

[75] Inventor: Donald N. Mehl, Chanhassen, Minn.

[73] Assignee: Creative Research & Manufacturing, Minneapolis, Minn.

[21] Appl. No.: 426,767

[22] Filed: Oct. 26, 1989

[51] Int. Cl.$^5$ .............................................. A61B 10/00
[52] U.S. Cl. ..................................... 128/754; 606/170
[58] Field of Search ............... 128/749, 751, 752, 753, 128/754, 305, 310; 606/167, 168, 170, 171

[56] References Cited

U.S. PATENT DOCUMENTS 4,667,684 5/1987 Leigh .................................. 128/754

Primary Examiner—Alan Cannon
Assistant Examiner—Randy Shay
Attorney, Agent, or Firm—Hugh D. Jaeger

[57] ABSTRACT

Tissue needle for extracting a biopsy sample including a pistol style squeezable hand grip for single hand tissue needle operation during a biopsy procedure. A spring tensioned sliding cannula, including a configured cutting edge, is actuated by a squeeze trigger and cam arrangement to slide over a fixed position stylet for entry into a tissue sample area. A squeeze trigger manually cycles using one hand to obtain a biopsy sample contained in a tissue sample notch of the sharp stylet tip whereupon the tissue needle can then be manually withdrawn. The tissue needle can be left temporarily in position in the tissue sample area in preparation for additional sampling while the stylet is withdrawn independently of the cannula prior to other samplings after subsequent reinsertion of the stylet into the cannula.

4 Claims, 13 Drawing Sheets

FIG. 21C POSITION "X" END VIEW

FIG. 21D POSITION "Y" REF.

4,976,269

TISSUE NEEDLE

BACKGROUND OF THE INVENTION

1. Field of the Invention

The present invention relates to a tissue sampling device, and more importantly, pertains to a single hand operation tissue needle for a biopsy.

2. Description of the Prior Art

Prior art biopsy needles utilize a cannula and a stylet which are both operated using different actuating members. Once the needle was inserted, extreme care has to be taken to insure that the proper actuator member moves in the proper sequence so that the needle member will not access the wrong tissue area, or move inadvertently past or out of the desired biopsy tissue area causing irritation or puncturing of an undesired tissue area. Often the user practitioner, due to unfamiliarity with the needle or procedure, would operate the needle members in an opposite and undesired direction, causing undue stress and trauma in, at or about adjacent tissue areas. Very detailed operational instructions were often hard to follow and required practice on the part of the practitioner, sometimes at the expense of a patient. Another problem was that in having two operating members, two hands were required for proper action of the prior art tissue needles when obtaining a biopsy sample. When additional tissue samples were required, the surgeon attempted, and not always successfully, to insert the biopsy needle into and further within the same puncture hole to obtain another deeper sample. Of course, if alignment with the puncture hole was not obtained, additional tissue damage occurred during the second biopsy procedure.

U.S. Pat. No. 4,667,684 issued to Leigh teaches a pistol grip biopsy device which is designed to be held in one hand by the physician during use. In operation, the Leigh device is substantially complicated, however because of the necessity to manually lock the stylet proximally using the movable hub before the device is advanced into the tissue. Similarly, the hub must be moved again to reextend the stylet to take a sample, and may need to be moved proximally again to permit removal. Even though this movement results in a removable stylet, use of the device probably necessitates control by both hands in many patients.

U.S. Pat. No. 4,733,671 issued to Mehl, the inventor of the present invention, teaches a tissue needle which truly provides one hand operation. Unfortunately, the Mehl device does not have a removable stylet to permit multiple samples to be taken without repositioning the outer cannula.

The present invention overcomes the disadvantages of the prior art by providing a tissue needle requiring single-handed operation at the biopsy point and having a removable stylet.

SUMMARY OF THE INVENTION

The general purpose of the present invention is a single-handed, manually operated biopsy needle with a removable stylet.

According to one embodiment of the present invention, there is provided a pistol grip tissue needle for biopsy wherein a sliding cannula, including a configured sliding edge, positions co-axially to slide over a removable stylet. A squeeze trigger actuates a linkage arm to cause a linkage block and the attached cannula to slide over the stylet to excise a biopsy sample contained in a tissue sample notch. A return spring returns the cannula to an unactuated position when pressure upon the squeeze trigger is released. A slide containment member secures the stylet within the sliding cannula.

One significant aspect and feature of the tissue needle, the present invention, is a tissue needle requiring physical actuation of a single member to obtain a core tissue sample. The tissue needle includes a fixed position needle sharp stylet positioned in a gripping handle, and a cannula which slides over the stylet. The cannula is spring-biased for return to a home position.

Another significant aspect and feature of the present invention is a tissue needle requiring only one hand for proper operation. The cannula is actuated by a linkage arm connected to a squeeze trigger actuator bar arrangement. A removable stylet is held in place by a sliding containment member.

A further significant aspect and feature of the present invention is a handle contoured to a user's hand.

Having thus described the principal embodiments of the present invention, it is a principal object hereof to provide a tissue needle.

One object of the present invention is to provide a tissue needle operable by one hand whereby only a trigger squeezing action is required.

Another object of the present invention is a removable stylet for removing the tissue sample.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 21A-21E illustrate stylet cutting surfaces.

DESCRIPTION OF THE PREFERRED EMBODIMENTS

Figure 1:
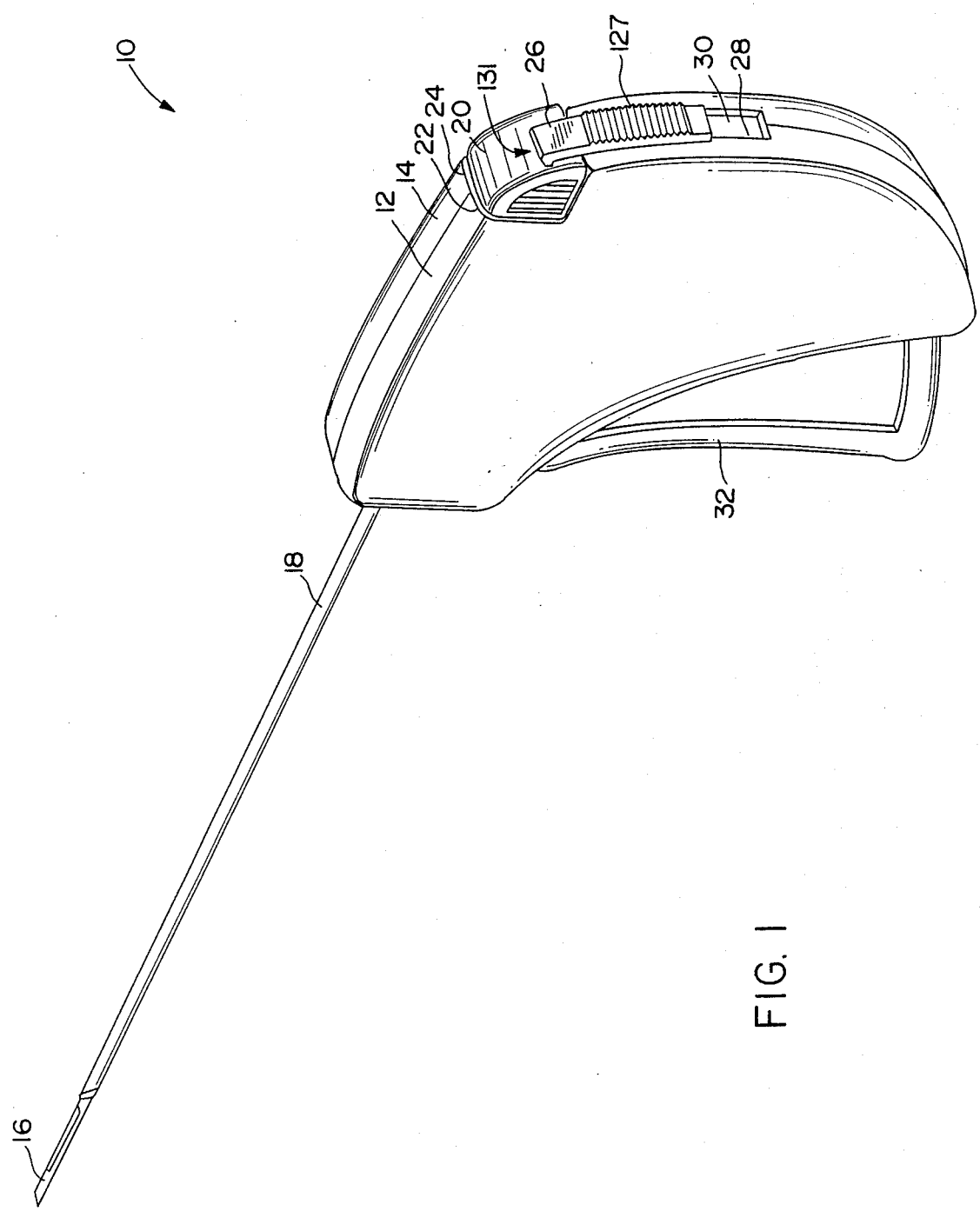
FIG. 1 illustrates a perspective view of the tissue needle, the present invention.

FIG. 1 illustrates a perspective view of the tissue needle 10, the present invention, including handle halves 12 and 14, a removable stylet 16, a sliding cannula 18 mounted coaxially to the removable stylet 16, and a gripping member 20 secured at one end of the removable stylet 16 and residing in cutouts 22 and 24 in handle halves 12 and 14. A sliding containment member 26 slides in recess halves 28 and 30 along the rear side of the handle half 12 to contain the gripping member 20 and the attached removable stylet 16 within the tissue needle 10 in general and specifically within the sliding cannula 18. A trigger or actuator bar 32 positions and pivots between the handle halves 12 and 14 to actuate the sliding cannula 18.

Figure 2:
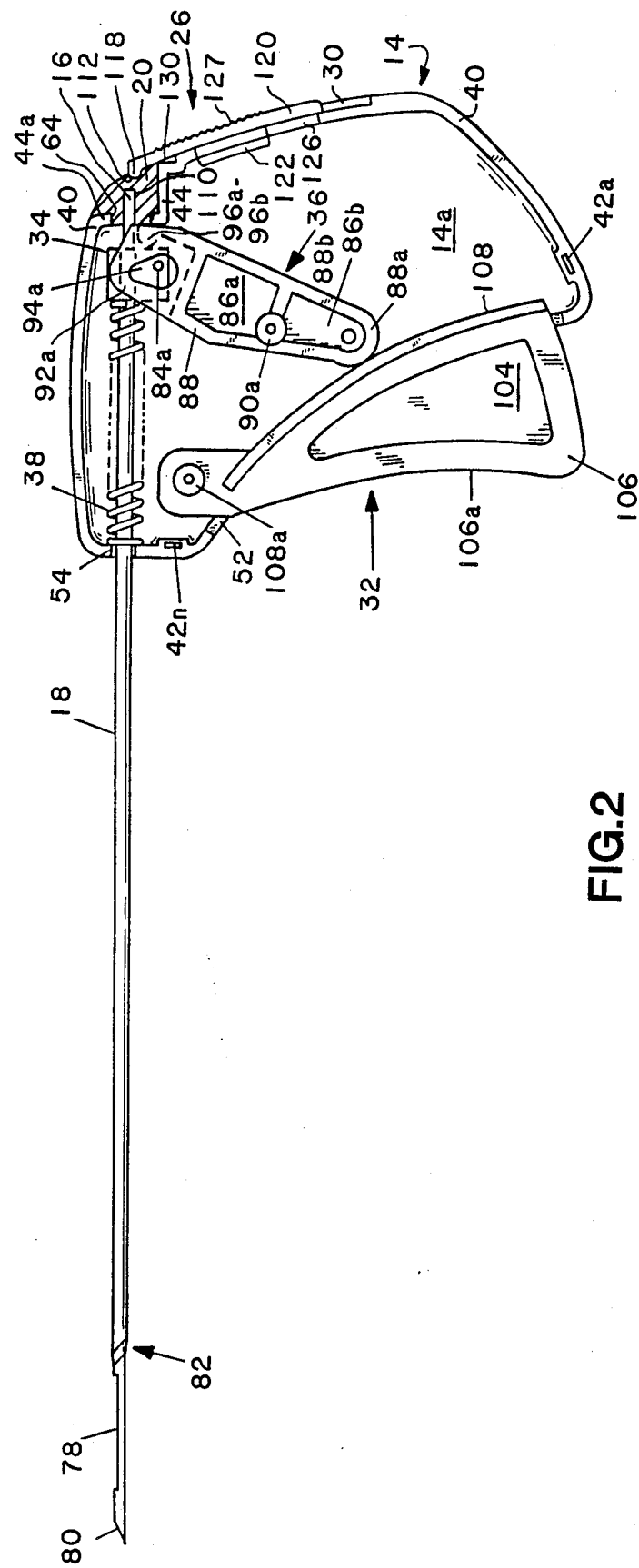
FIG. 2 illustrates a side elevation of a tissue needle.
Figure 5:
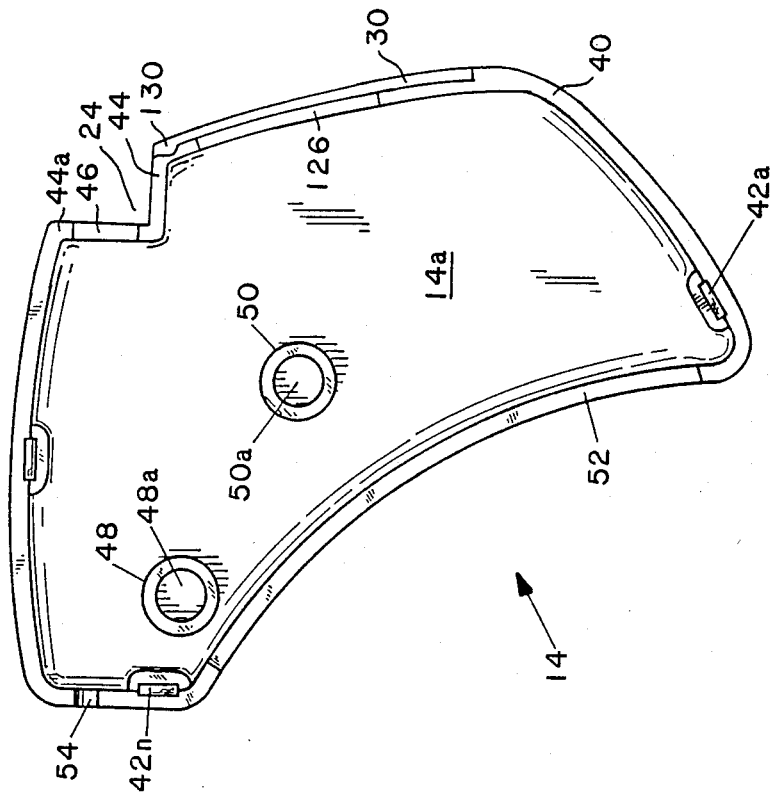
FIGS. 5 illustrates a side elevation of the right tissue needle handle.
Figure 6:
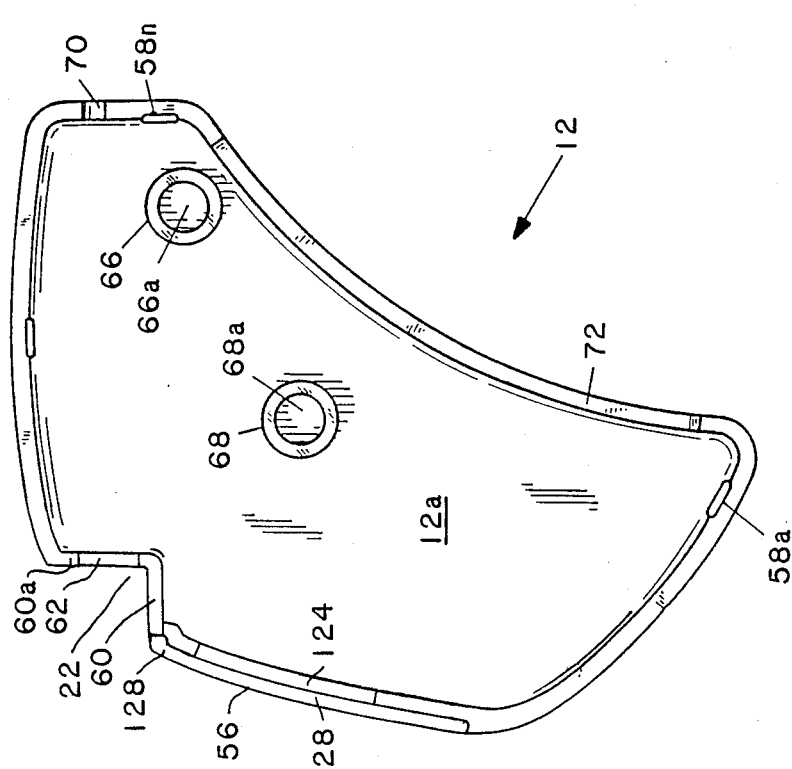
FIG. 6 illustrates a side elevation of the left tissue needle handle.
Figure 19:
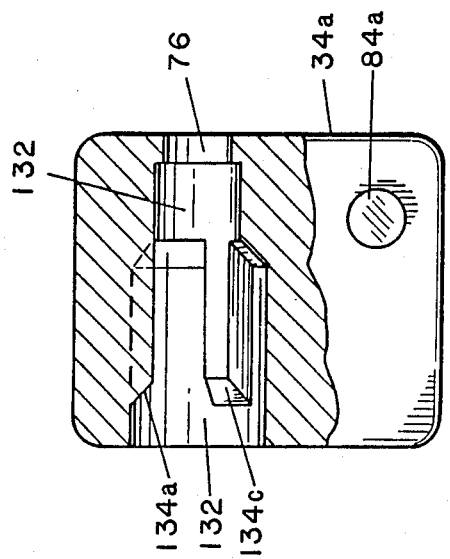
FIG. 19 illustrates a partial cross section taken along line 19—19 of FIG. 18.

FIG. 2 illustrates a side elevation view of a tissue needle 10 the present invention where handle half 12 is removed for purposes of illustration. The tissue needle 10 includes handle halves 12 and 14, also illustrated in FIG. 1, a removable stylet 16, a sliding cannula 18 mounted coaxially to removable stylet 16, a linkage block 34, a linkage arm 36, a trigger or actuator bar 32, and a compression spring 38 mounted over and about the sliding cannula 18 where all elements position in or affix to handle half 14 as illustrated in the figure. Handle half 14, also illustrated in FIG. 5, includes handle half surface 14a, raised edge member 40, alignment slots 42a-42n adjacent to and inwardly from the raised edge member 40, and a raised right angle member 44 affixed to and of corresponding height to the affixed raised edge member 40, and including a half hole 46 in the vertical surface 44a of the raised right angle member 44. A pivot bar member 48 projects inwardly from the handle half surface 14a and includes a pivot hole 48a, a raised cylindrical pivot member 50 projecting inwardly from the handle half surface 14a and including a pivot hole 50a, and an actuator bar cutout 52 for accommodation of the pivot bar member 48, each of which is illustrated in FIG. 5. A half hole 54, slightly larger than the sliding cannula 18, positions in the upper left portion of raised edge member 40 for sliding accommodation of the sliding cannula 18. The like and opposite mirror image handle half 12, as also illustrated in FIG. 6, positions over and about the handle half 14. The handle half 12, illustrated in FIG. 6, includes a handle half surface 12a, a raised edge 56, and alignment tabs 58a-58n adjacent to and projecting outwardly from the raised edge 56 for engagement with alignment slots 42a-42n in the handle half 14. A raised right angle member 60 corresponding to the raised right angle member 44 in the handle half 14 both align loosely over the radius portion 64 of the gripping member 20 to engage their respective half holes 46 and 62 of the handle halves 12 and 14, thus loosely aligning the radius portion 64 of the gripping member 20 and thus the removable stylet 16 between and within the half holes 46 and 62. As illustrated in FIG. 6, a pivot bar member 66 projects inwardly from handle half surface 12a and includes a pivot hole 66a, and a cylindrical pivot member 68 projecting inwardly from the handle half surface 14a and includes pivot hole 68a. A sliding cannula accommodation hole 70, slightly larger than the sliding cannula 18, and actuator bar cutout 72 which corresponds to like elements 54 and 52 in the handle half 14 position in the raised edge 56 of the handle half 12 as illustrated in FIG. 6. The removable stylet 16 positions interiorly and coaxially within a cylindrical cavity 74 of the sliding cannula 18 and also passes through a hole 76 in the linkage block 34, as described in FIG. 17. A flat ground tissue sample notch 78 positions longitudinally in close proximity to a compound cut tip 80 described later in detail in the figures. The sliding cannula 18 and the linkage block 34 slide laterally along the removable stylet 16 and against the compression spring 38. The opposite end of the compression spring 38 positions against the raised edges 40 and 56 in the area of the half holes 54 and accommodation hole 70. One end of the sliding cannula 18 positions in and is secured within the linkage block 34, as described later in detail in FIG. 17. The other end of the sliding cannula 18, near the compound cut tip 80 includes a tissue cutting tip 82 as later described in detail in FIGS. 12A-21E. Actuating pins 84a and 84b are positioned on the lower portion of the vertical sides 34a and 34b of the linkage block 34 to assure the alignment of linkage block 34 and the sliding cannula 18, and provides secure attachment of the linkage block 34 to the linkage arm 36 as also illustrated in FIGS. 18 and 19.

Figure 7:
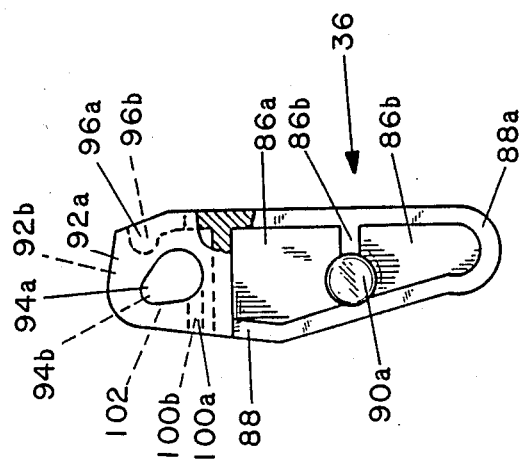
FIG. 7 illustrates a side view of the linkage arm.
Figure 8:
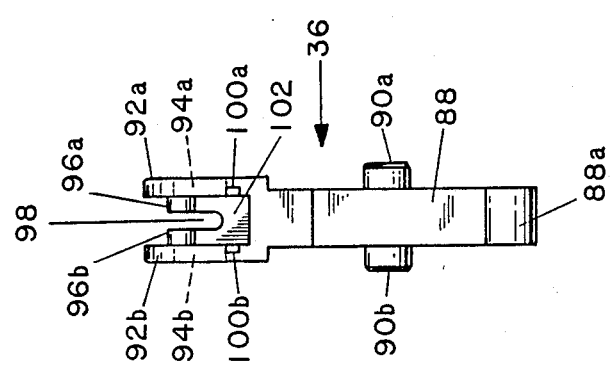
FIG. 8 illustrates an end view of the linkage arm.

Configured linkage arm 36, also illustrated in FIGS. 7 and 8, includes planar midsections 86a and 86b, a raised edge 88, a rounded raised edge 88a, a raised edge 88b dividing the planar midsections 86a and 86b, cylindrical pivot points 90a and 90b and upper opposed mirror image planar sides 92a and 92b. As illustrated in FIGS. 7 and 8, dual radius cam holes 94a and 94b position as illustrated in the planar sides 92a and 92b to accommodate the actuating pins 84a and 84b of the linkage block 34 illustrated in FIG. 18. Linkage block actuator cams 96a and 96b and a slot 98 disposed therebetween position between the planar sides 92a and 92b as illustrated in FIGS. 7 and 8. Slot 98 accommodates the removable stylet 16 during the operational mode of the tissue needle 10. Small positioning slots 100a and 100b illustrated in FIGS. 7 and 8 position interiorly to the planar sides 92a and 92b for accommodation of the actuating pins 84a and 84b during assembly of the tissue needle. Cavity 102 shown in FIGS. 7 and 8 positions interiorly to the planar sides 92a and 92b to accommodate the linkage block 34. Cylindrical pivot points 90a and 90b position in the pivot members 50 and 68 of the handle halves 14 and 12, respectively. The trigger or actuator bar 32 contacts the rounded raised portion 88a of the linkage arm 36 to cause rotational movement of the linkage arm 36 in a counter-clockwise fashion about pivot points 90a and 90b, and actuation of the sliding cannula 18 along the removable stylet 16. The trigger or actuator bar 32 includes an inner planar member 104, an outer planar member 106, thicker and heavier with respect to the inner planar member 104, and includes an arced finger grip surface or manual actuating surface 106a which conforms to the actuator bar cutouts 52 and 72 of the handle halves 14 and 12. Pivot point members 108a and 108b oppose each other on the manual actuating surfaces 106c and 106d of the outer planar member 106, and position in the pivot bar members 66 and 48. A radiused or arced linkage arm actuator member 108 positions perpendicularly to the outer planar member 106, and is essentially a substantially rectangular member which conforms to the curvature of the outer planar member 106.

Figure 4:
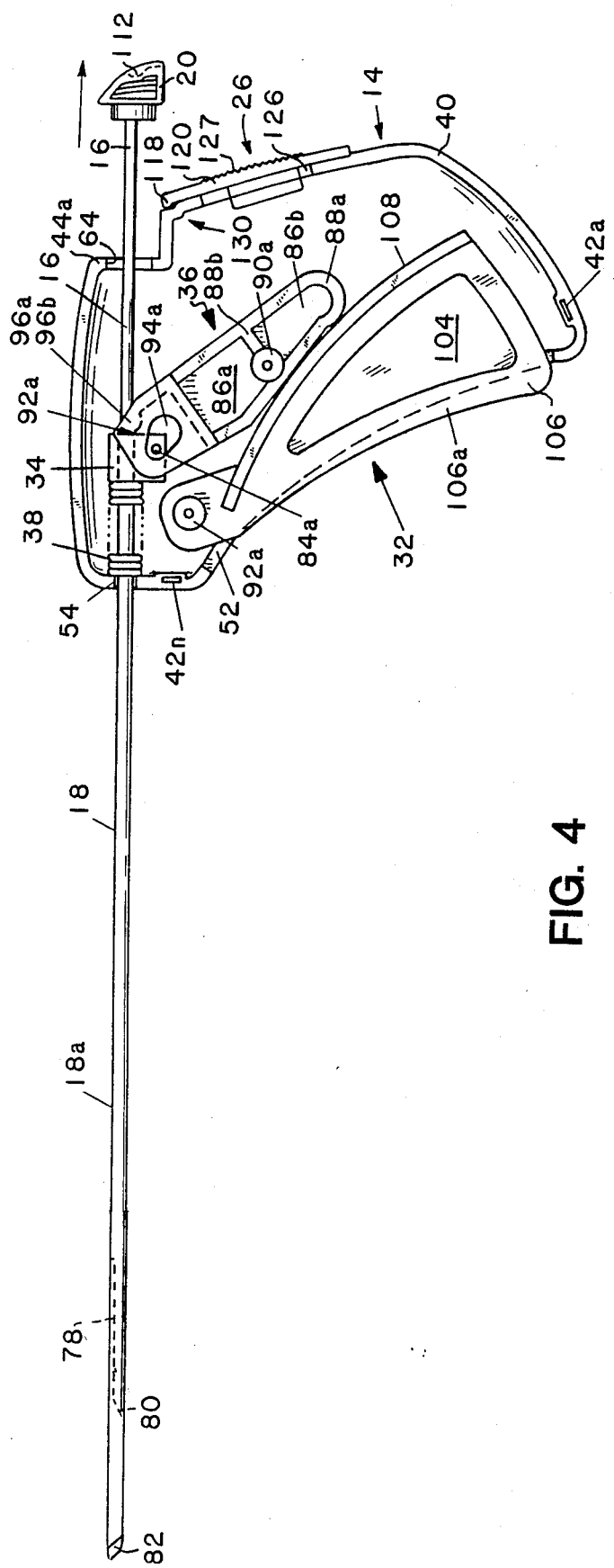
Figure 11:
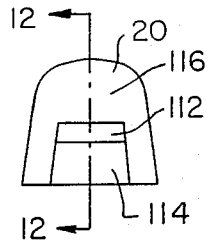
FIG. 11 illustrates an end view of the gripping member.
Figure 12:
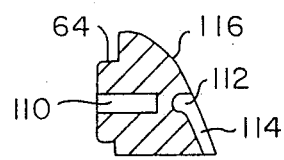
FIG. 12 illustrates a side view in cross section taken along line 12—12 of FIG. 11.
Figure 14:
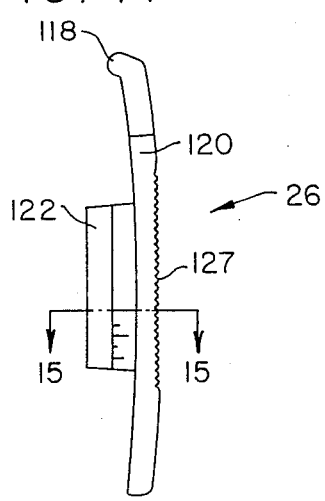
FIG. 14 illustrates a side view of the sliding containment member.
Figure 16:
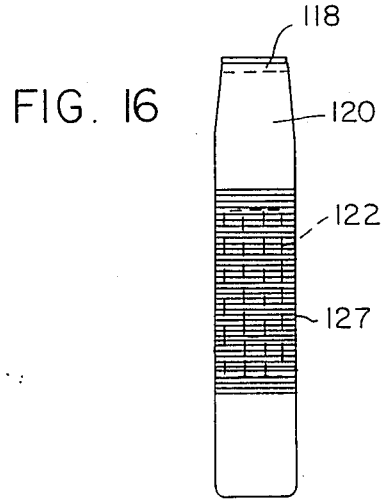
FIG. 16 illustrate an end View of the sliding containment member.

The gripping member 20, also illustrated in FIGS. 4, 11 and 12, resides in and conforms to the shape of the cutouts 22 and 24 as illustrated in FIG. 1. The removable stylet 16 secures in a hole 110. A horizontal groove 112 and a planar recess 114 on the rear curved surface 116 of the gripping member 20 accommodate a horizontal cam 118 and the planar member 120 of the sliding containment member 26 as also illustrated in FIGS. 14 and 16. The sliding containment member 26 is positionable along and within recess halves 28 and 30 to retain the gripping member 20 and removable stylet 16 within the sliding cannula 18 and the cutouts 22 and 24, respectively. A "T" member 122 extends perpendicularly from the planar member 120. The "T" member 122 is captured in slot halves 124 and 126 which are located adjacent to and inwardly from the recess halves 28 and 30 in the handle halves 12 and 14. The sliding containment member 26 includes a groove finger grip surface 127. The planar member 120 and the "T" member 122 are arced slightly to conform to the curvature of the recess halves 28 and 30. In addition, detent halves 128 and 130 which form a detent 131 are located at the intersection of the horizontal portion of the raised right angle members 60 and 44 and the upper ends of the recess halves 28 and 30 to lock the sliding containment member 26 out of the way for ease of removal of the removable stylet 1 and attached gripping member 20, as illustrated in FIG. 4.

FIG. 5 illustrates a side elevation of the right handle half 14 where all numerals correspond to those elements previously described Shown in particular are the half hole 54, the half hole 46 in the raised right angle member 44, and the pivot bar members 48 and 68. The exterior surface of both handle halves 12 and 14 can be textured to provide a superior gripping surface on each side of the handle halves.

FIG. 6 illustrates a side elevation of the left handle half 12 where all numerals correspond to those elements previously described. Shown in particular in this illustration are members corresponding to the right handle including the sliding cannula accommodation hole 70, the pivot bar members 66 and 68, and the alignment tabs 58a–58n which align with alignment slots 42a–42n of handle half 14 of FIG. 5.

FIG. 7 illustrates a side view of the linkage arm 36 where all numerals correspond to those elements previously described. Shown in particular is the orientation of the dual radius cam holes 94a–94b which allow proper capture of the actuating pins 84a–84b when the dual radius cam holes 94a–94b move in an arc during actuation of the linkage arm 36.

FIG. 8 illustrates an end view of the linkage arm 36 where all numerals correspond to those elements previously described. The cavity 102 is shown between the planar sides 92a and 92b for accommodation of the linkage block 34. The slot 98 between the linkage block actuator cam 96a and 96b accommodates the removable stylet 16 as the linkage arm 36 travels in an arcular path during cannula actuation.

Figure 9:
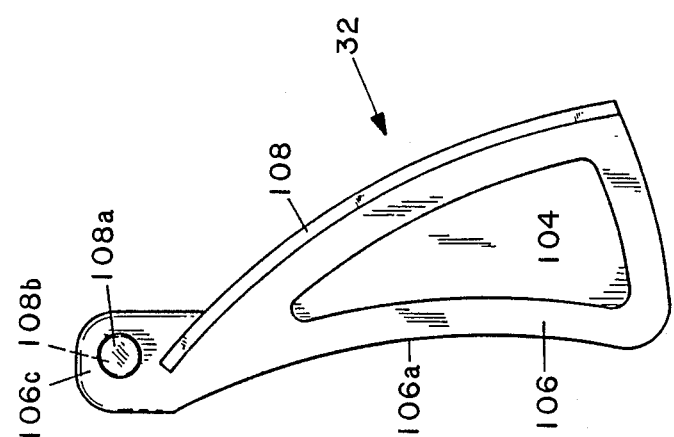
FIG. 9 illustrates side view of the actuator bar.

FIG. 9 illustrates a side view of the trigger or actuator bar 32 where all numerals correspond to those elements previously described.

Figure 10:
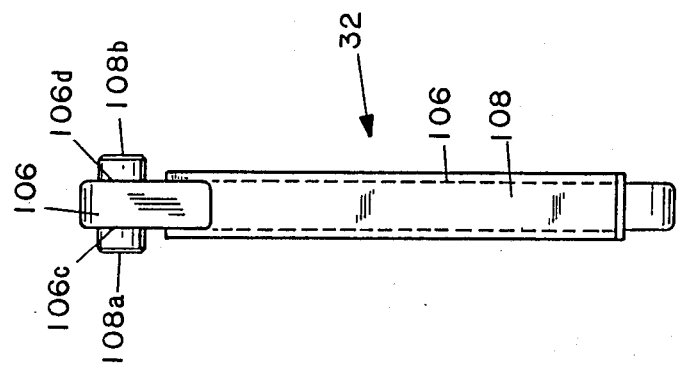
FIG. 10 illustrates an end view of the actuator bar.

FIG. 10 illustrates an end view of the actuator bar 32 where all numerals correspond to those elements previously described. Shown in particular are the pivot point members 108a and 108b positioned on the opposing faces 106c and 106d of the configured outer planar member 106.

FIG 11 illustrates an end view of the gripping member 20 where all numerals correspond to those elements previously described. Illustrated in particular is the planar recess 114 and the horizontal groove 112 set into the upper surface of the planar recess 114 for accommodation of the horizontal cam 118 and the upper portion of the planar member 120 of the sliding containment member 26.

FIG 12 illustrates a side view in cross section taken along line 12—12 of FIG. 11 where all numerals correspond to those elements previously described. Illustrated in particular are the planar recess 114 and the horizontal groove 112 at the upper portion of the planar recess 114.

Figure 13:
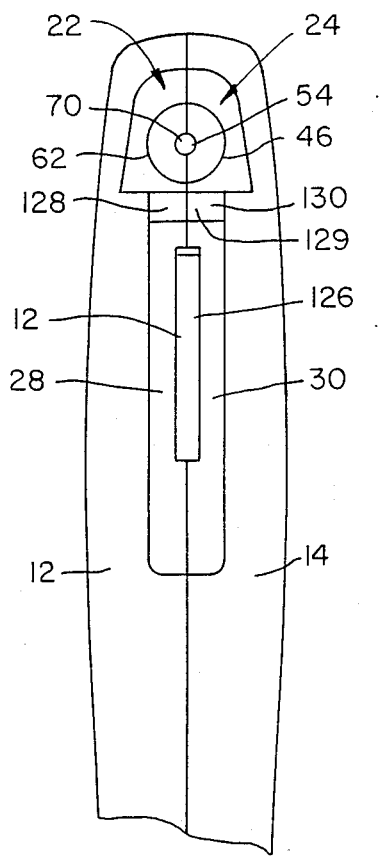
FIG. 13 illustrates an end view of the handle halves.

FIG. 13 illustrates an end view of the handle halves 12 and 14 where all numerals correspond to those elements previously described Illustrated in particular are the recess halves 28 and 30 and the slot halves 124 and 126 adjacent to the recessed halves 28 and 30. Detent slot halves 128 and 130 align to form a wide detent 131.

Figure 15:
FIG. 15 illustrates a cross-sectional view of the sliding containment member taken along line 15—15 of FIG. 14.

FIG. 14 illustrates a side view of the sliding containment member 26 where all numerals correspond to those elements previously described FIG. 15 illustrates a cross-sectional view of the sliding containment member 26 along line 15—15 of FIG. 14 where all numerals correspond to those elements previously described.

Figure 17:
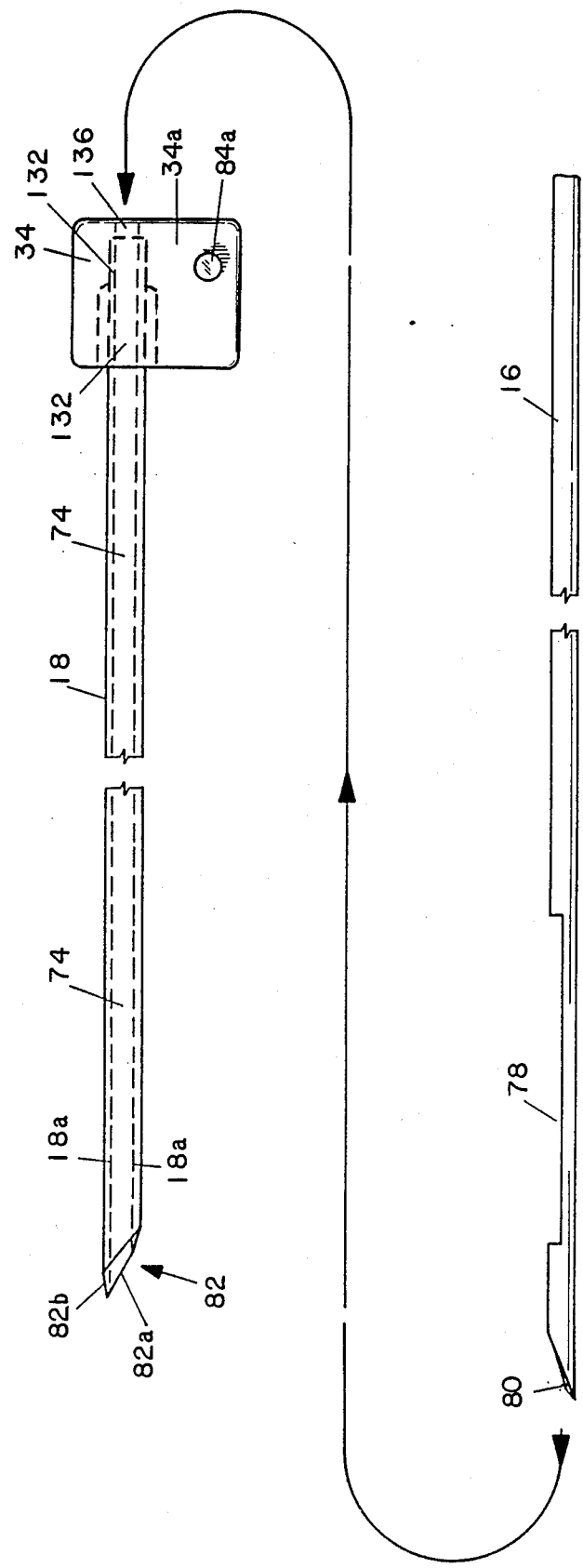
FIG. 17 illustrates a side view of the linkage block.
Figure 18:
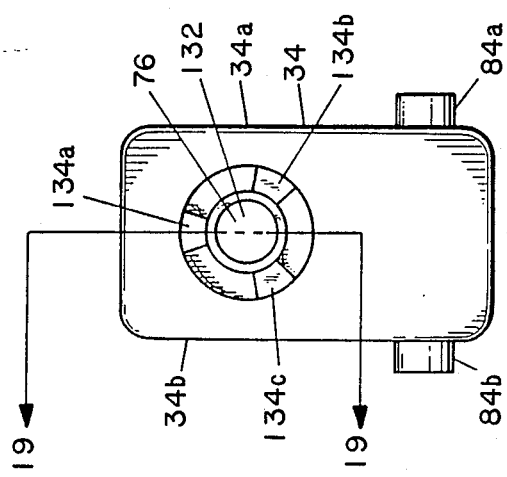
FIG. 18 illustrates an end VieW of the linkage block.

FIG. 16 illustrates a top view of the sliding containment member 26 where all numerals correspond to those elements previously described FIG. 17 illustrates a side view of the linkage block 34, the removable stylet 16, and the sliding cannula 18 where all numerals correspond to those elements previously described An end of the sliding cannula 18 is cemented or otherwise likely secured in the dual radiused hole 132 in the linkage block 34. Ribs 134a, 134b and 134c, as illustrated in FIGS. 18 and 19, position about the larger inner circumference of the dual radiused hole 132 to position and support the end of the sliding cannula lB in the dual radiused hole 132. A bonding agent is applied between the ribs 134a–134c to secure the sliding cannula 18 within the dual radiused hole 132. Another hole 136 in the linkage block 34 aligns with the hole 132 to permit entry of the removable stylet 16 into the cylindrical cavity 74 in the center of sliding cannula 18. The angled cutting tip 82 is cut on a bias 82b to effect the ellipsoid cutting edge 82a. Biasing of the tissue cutting tip 82 allows for streamlined comfortable entry into the tissue sample area.

FIG. 18 illustrates an end view of the linkage block 34 where all numerals correspond to those elements previously described The ribs 134a–134c are shown positioned radially about the large diameter of the dual radiused hole 132.

FIG. 19 illustrates a partial cross section taken along line 19—19 of FIG. 18 where all numerals correspond to those elements previously described. The ribs 134a and 134c are illustrated positioned in the dual radius hole 132.

Figure 20:
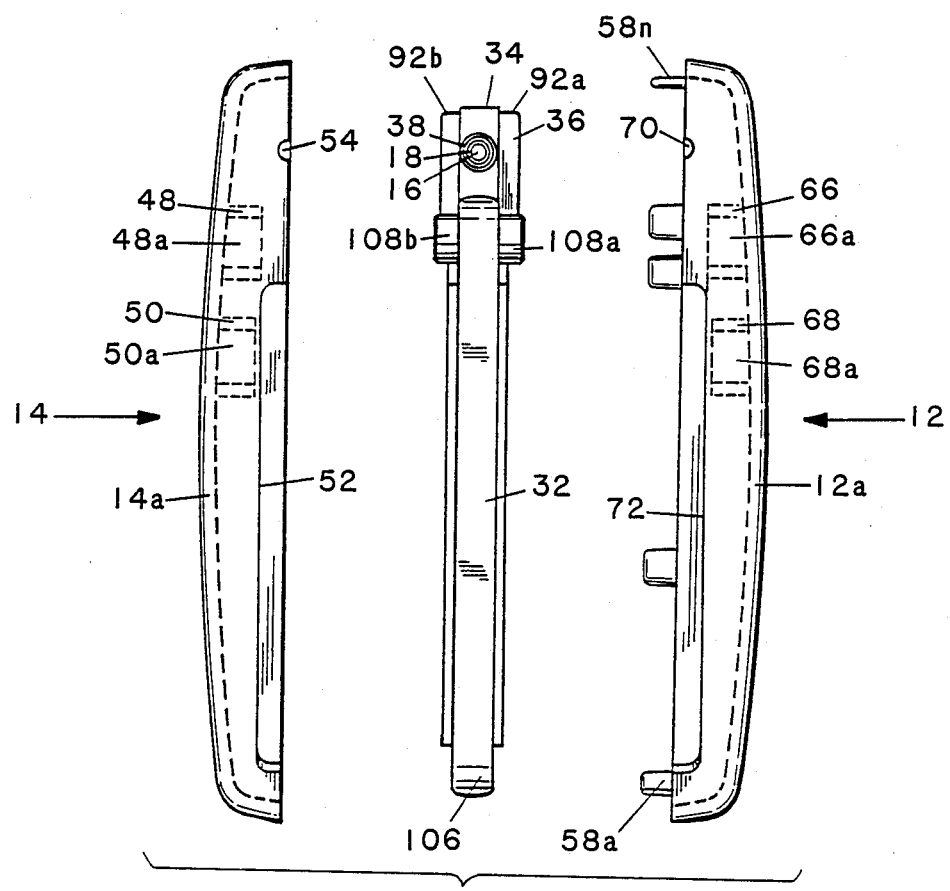
FIG. 20 illustrates an exploded end view of the handle halves.
Figure 21A:
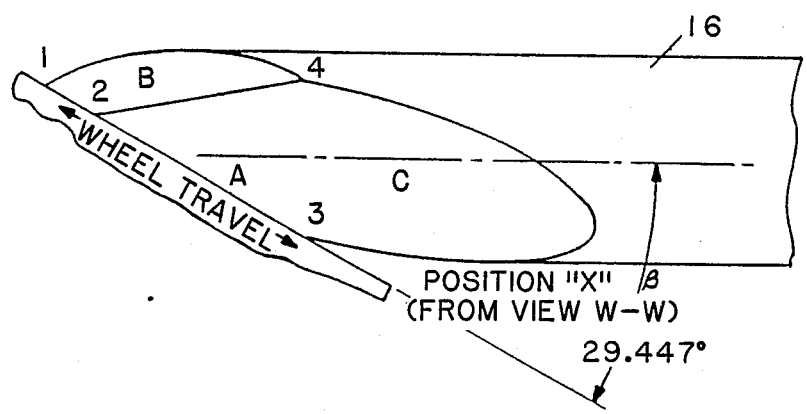
Figure 21B:
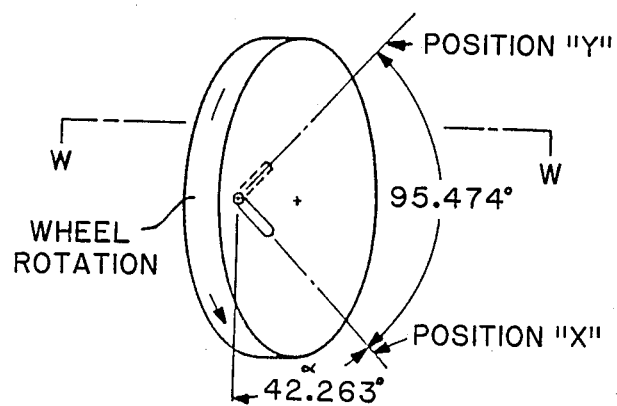
Figure 21E:
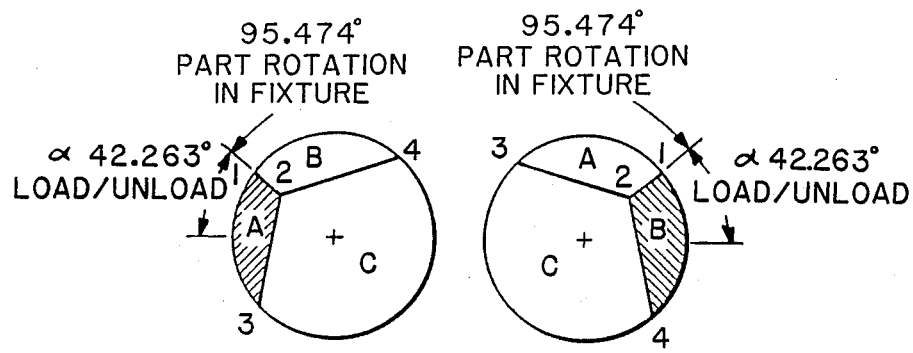
Figure 21E:
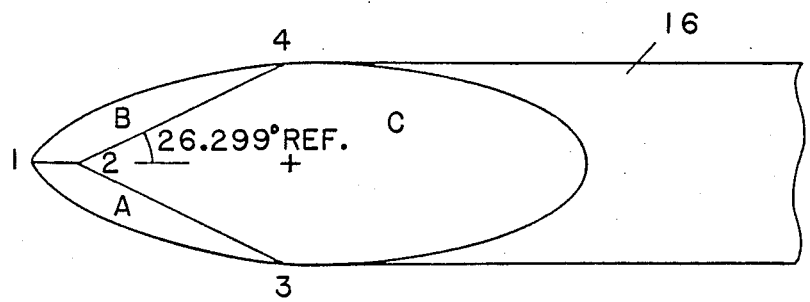

FIG. 20 illustrates an exploded end view of the handle halves 12 and 14, the linkage block 34, the linkage arm 36 and the actuator bar 32 prior to assembly where all numerals correspond to those elements previously described. FIG. 21A–21E illustrate stylet cutting surfaces where all numerals correspond to those elements previously described. FIG. 21A illustrates positioning with respect to a grinding wheel. FIG. 21B illustrates the angle of approach to the grinding wheel. FIGS. 21C and 21D illustrate the angle of rotation to cut both cutting surfaces. FIG. 21E illustrates the finished stylet cutting surface.

The surface references of the tip are as follows: Established angle so that:

$$\frac{SIN\ (.032) + COS\ (.032)}{.08007} = \frac{SIN\ (.01914) + COS\ (.032)}{.06475}$$

$$\text{Then angle} = TAN^{-1}\frac{SIN\ (.032) + COS\ (.032)}{.08007}$$

MODE OF OPERATION

Figure 3:
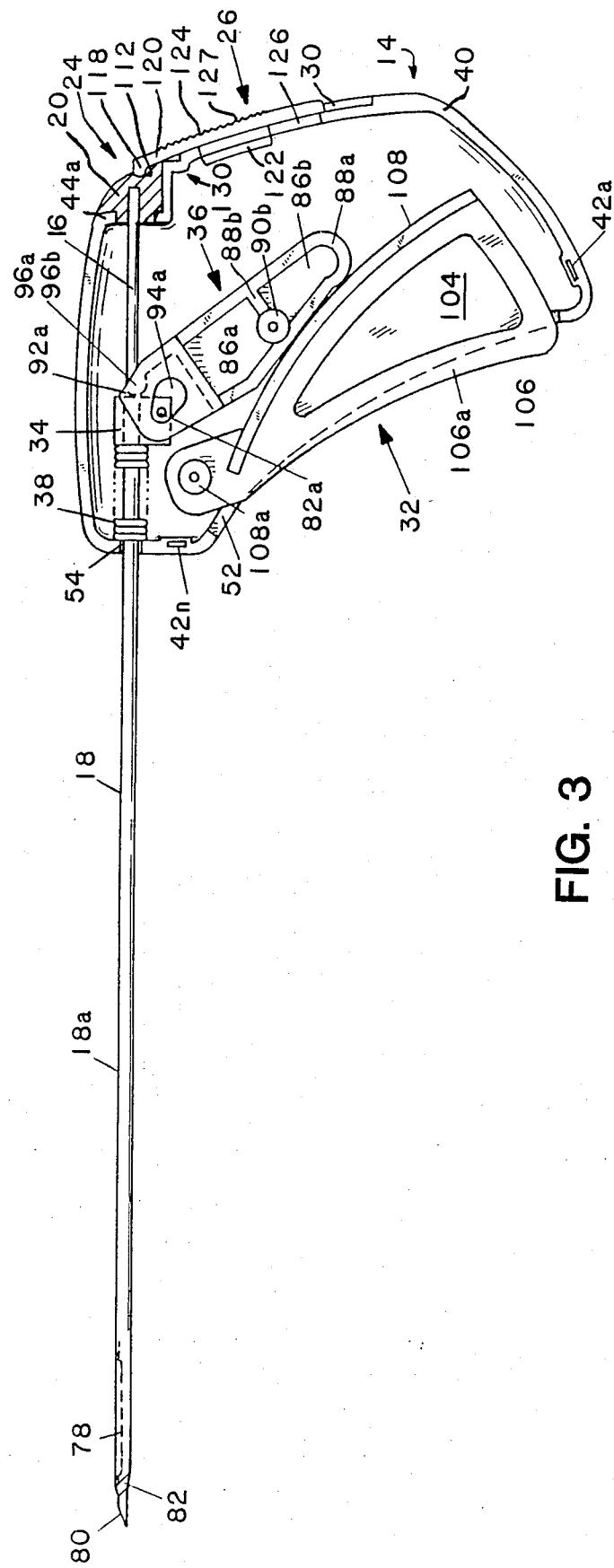
FIGS. 3 and 4 illustrate a side elevation of a tissue needle in a operational mode.

FIGS. 3 and 4 illustrate a side elevation of the tissue needle 10, and the mode of operation where all numerals correspond to those elements previously described.

Prior to entry of the tissue needle 10 into the biopsy area, the trigger or actuator bar 32 is depressed manually by the surgeon as illustrated in FIG. 3. The arced actuator member 108 contacts against the rounded raised edge 88a causing the linkage arm 36 to rotate in a counter-clockwise fashion to slide the linkage block 34 and the sliding cannula 18 laterally along the removable stylet 16. Upon full depression of the trigger or actuator bar 32, the cutting tip 82 of the sliding cannula 18 encompasses and fully encloses the tissue sample notch 78 within the confines of the cylindrical walls of the sliding cannula 18 as illustrated. The bias-cut cannula cutting tip 82 positions adjacent to the stylet tip 80 to form a streamlined low profile point for entry into the biopsy area.

The surgeon now holds the tissue needle 10 with one hand, and causes, through force, the removable stylet 16 and cannula 18 to enter the biopsy tissue area. After entry to the tissue area, the trigger or actuator bar 32 is released while holding the handle halves 12 and 14 in the same relative position to the tissue. The sliding cannula 18 returns by action of the compression spring 38 against the linkage block 34 and retracts the cannula fully inwardly to the position illustrated in FIG. 2, exposing the tissue sample notch 78 whereupon tissue sample naturally enters the sample notch 78. The surgeon then depresses the trigger or actuator bar 32 to cause the sliding cannula 18 and the biased-cut cutting tip 82 to traverse the removable stylet 16, and cut a plug or like amount of tissue sample that is captured within the sample notch and within the portion of the cannula wall 18a that overlies the sample notch 78 as positioned in FIG. 3.

At this time a single sample may be obtained by removing the entire tissue needle 10 or the cannula may be left in a stationary position and a plurality of samples can be obtained. When a single sample is required, the following procedure is accomplished. With the tissue sample contained in the sample notch 78 and all elements position as in FIG. 3, the tissue needle 10 is withdrawn from the area the tissue sample is taken from with the actuator bar depressed. Upon removal, the trigger or actuator bar 32 is released and the sliding cannula 18 is retracted exposing the sample tissue contained in the tissue sample notch 78 so that the tissue sample may be removed from the tissue needle 10 for laboratory analysis.

It is noted that only one hand is required for complete operation of the tissue needle 10 itself, leaving the surgeons other hand free to provide support or external manipulation as needed about the biopsy area as required.

To obtain a plurality of samples the following method of operation is executed. Where the first plug of sample tissue has been cut and captured in the sample notch 78 and when the tissue needle 10 is positioned as in FIG. 3 with the actuator bar still depressed, the surgeon then slidingly positions the sliding containment member 26 downwardly within the recess halves 28 and 30, thus disengaging the horizontal cam 118 from the horizontal groove 112 in the gripping member 20. The horizontal cam 118 snaps into the detent halves 128 and 130 of the wide detent 131 to secure the sliding containment member 26 in a position free and clear of the cutout areas 22 and 24. This action allows for free movement of the gripping member 20 and the attached removable stylet 16 by the surgeon. The gripping member 20 is grasped by the surgeon, and the removable stylet 16 and a first tissue sample contained in the notch 78 of the removable stylet 16 is removed by disengagement from the sliding cannula 18. The tissue sample is then removed from the notch 78 and the removable stylet 16 is then reinserted into the sliding cannula 18. The sliding containment member 26 is then positioned over the gripping member 20 to secure the removable stylet 16 within the sliding cannula 18 in the position as illustrated in FIG. 3. With the trigger actuator bar 32 still depressed, the surgeon then moves the tissue needle 10 with the secured removable style 16 further through the existing puncture and deeper into the tissue area to obtain a second tissue sample. The trigger actuator bar 32 is then relaxed to allow the sliding cannula 18 to retract and expose the notch 78 to receive tissue. The trigger actuator bar 32 is then depressed to sever the tissue in the notch 78 and to contain the tissue in the notch 78. The removable stylet 16 and new tissue sample contained in the notch 78 are then removed as previously described. When the final tissue sample has been obtained, the tissue needle 10 is then withdrawn with the trigger actuator bar 32 still depressed. The tissue needle 10 can be withdrawn with the removable stylet 16 secured within the sliding cannula 18 or with the removable stylet 16 external to the sliding cannula 18.

Various modification can be made to the present invention without departing from the apparent scope hereof.

I claim:

1. Apparatus for obtaining a tissue sample comprising:
   a. a housing having a front face and an opposite rear face;
   b. a cannula having a proximal end and a distal end wherein said proximal end is slidably affixed to said housing and protruding from said front face of said housing and said distal end is sharpened to puncture tissue;
   c. a stylet slidably located within said cannula having a distal end with means for holding said tissue sample and proximal end removably attached to said housing and removable from said rear face of said housing;
   d. means on said front face responsively coupled to said cannula and responsive to a control force in a first direction for advancing said cannula and for returning said cannula to a retracted position in response to removal of said control force in said first direction; and,
   e. means slidably located on said rear face of said housing for locking said stylet to prevent movement with respect to said housing when in a first position and for releasing said stylet to permit removal from said housing when in a second position.

2. Apparatus according to claim 1 wherein said holding means comprises a tissue notch.

3. Apparatus according to claim 2 wherein said housing further comprises a hand conforming grip.

4. Apparatus according to claim 3 wherein said retracting and advancing and returning means further comprises a trigger.

* * * * *